United States Patent
Kadokura et al.

(10) Patent No.: US 6,426,425 B2
(45) Date of Patent: Jul. 30, 2002

(54) PROCESS FOR PURIFYING GALLIUM ALKOXIDE

(75) Inventors: Hidekimi Kadokura, Tokyo; Tadashi Ishii, Saitama-Ken, both of (JP)

(73) Assignee: Kabushikikaisha Kojundokagaku Kenkyusho, Tokyo (JP)

( * ) Notice: Subject to any disclaimer, the term of this patent is extended or adjusted under 35 U.S.C. 154(b) by 6 days.

(21) Appl. No.: 09/798,724

(22) Filed: Mar. 2, 2001

(30) Foreign Application Priority Data

Mar. 17, 2000 (JP) ......................................  2000-121763

(51) Int. Cl.$^7$ .................................................. C07F 5/00
(52) U.S. Cl. ........................................................... 556/1
(58) Field of Search ............................................... 556/1

(56) References Cited

U.S. PATENT DOCUMENTS

| | | | | |
|---|---|---|---|---|
| 3,062,857 A | * | 11/1962 | Acciarri et al. | 534/11 |
| 4,797,500 A | * | 1/1989 | Kadokura et al. | 556/1 |
| 5,470,555 A | * | 11/1995 | Shimada et al. | 260/665 R |
| 5,783,717 A | * | 7/1998 | Ohsaki et al. | 556/1 |

* cited by examiner

Primary Examiner—Porfirio Nazario-Gonzalez
(74) Attorney, Agent, or Firm—Fattibene & Fattibene; Paul A. Fattibene; Arthur T. Fattibene

(57) ABSTRACT

The invention provides a process for purifying gallium alkoxides by decreasing the amount of impurity chlorine contained therein, gallium alkoxides which are useful as raw materials for the formation of dielectrics containing gallium oxide and as raw materials for the syntheses of compounds for photoelectronics. Gallium isopropoxide containing 0.98 weight percent of chlorine and potassium isopropoxide of 1.4 equivalents to the impurity chlorine are refluxed in toluene as a solvent for 5 hours, the solvent is distilled away, and the residue is simply distilled under vacuum to obtain gallium isopropoxide containing 0.022 weight percent of the chlorine in a 89% yield.

5 Claims, No Drawings

PROCESS FOR PURIFYING GALLIUM ALKOXIDE

FIELD OF THE INVENTION

The present invention relates to a process for purifying gallium alkoxides useful for the formation of dielectrics containing gallium oxide and the syntheses of compounds for photoelectronics.

DESCRIPTION OF THE RELATED ART

The gallium alkoxides have been studied as raw materials for the formation of the dielectrics containing gallium oxide such as $NdGaO_3$ and $LaSrGaO_4$ and raw materials for the syntheses of the compounds for photoelectronics.

For the preparation of the gallium alkoxides, R. C. Mehrotra and R. K. Mehrotra, *Current Sci.* (India), Vol. 33 (8), 241 (1964) disclose a process for preparing gallium isopropoxide by reaction of sodium isopropoxide with gallium chloride in benzene solvent. The reaction of the gallium isopropoxide with other alcohols to allow the preparation of gallium methoxide, gallium ethoxide, gallium n-propoxide, gallium butoxide, and the like is disclosed by S. R. Bindal, V. K. Mathur, and R. C. Mehrotra, *J. Chem. Soc.*, A863 (1969).

As described above, in general, gallium isopropoxide (hereinafter represented by $Ga(OiPr)_3$) important as a starting material for the gallium alkoxides is prepared by the reaction of sodium isopropoxide (hereinafter represented by NaOiPr) with gallium chloride (hereinafter represented by $GaCl_3$).

However, there has been no known literature on the content of chlorine contained as an impurity in $Ga(OiPr)_3$ prepared by this process. The present inventors carried out the reaction of $GaCl_3$ with NaOiPr equivalent or more thereto, subsequently the recovery of the resulting $Ga(OiPr)_3$ by distillation, and the analysis of a chlorine content, and as a result found that the product is contaminated by approximately 1 weight percent of chlorine.

Parts for electronic elements contaminated by a chlorine impurity cause deterioration in the performances or lives thereof. Therefore, reduction in the chlorine content of the gallium alkoxides has been demanded. In particular, reduction in the chlorine content of $Ga(OiPr)_3$ that is a raw material for various compounds has been demanded.

SUMMARY OF THE INVENTION

The invention aims at providing a process for purifying the gallium alkoxides to reduce the content of a chlorine impurity.

The invention provides the process for purifying the gallium alkoxides characterized by adding potassium alkoxides to the gallium alkoxides containing chlorine compounds as impurities to allow both alkoxides to react in an organic solvent and subsequently recovering the gallium alkoxides by distillation or sublimation.

Furthermore, the invention provides the process for purifying gallium isopropoxide characterized by adding potassium isopropoxide to gallium isopropoxide containing chlorine compounds as impurities to allow both isopropoxides to react in an organic solvent and subsequently recovering gallium alkoxides by distillation.

In the invention the aforesaid process for purifying the gallium alkoxides is characterized in that the amount of the potassium alkoxides added ranges from 1 to 3 equivalent to the amount of the chlorine impurity.

In the invention the aforesaid process for purifying the gallium alkoxides is characterized in that the organic solvent used in the process is a compound selected from toluene, xylene, alkanes having 6 to 10 carbon atoms, and cycloalkanes having 6 to 10 carbon atoms.

DETAILED DESCRIPTION OF THE INVENTION

As an example, $Ga(OiPr)_3$ is described below. In a general process for producing $Ga(OiPr)_3$, $GaCl_3$ is allowed to react with NaOiPr equivalent or slightly excess equivalent to the chloride in benzene or toluene as a solvent at a reflux temperature. Subsequently, NaCl by-produced is separated by filtration, the solvent is distilled away, and finally $Ga(OiPr)_3$ is recovered by distillation. The distillation conditions are 1 Torr and approximately 120° C.

The inventors have carried out the analysis of $Ga(OiPr)_3$ prepared by the aforesaid process and found that the isopropoxide contains approximately 1 ppm of sodium and as much as 0.6 to 1.2 weight percent of chlorine.

The synthesis reaction of $Ga(OiPr)_3$ is shown by the following formulas.

$$GaCl_3+NaOiPr=GaCl_2(OiPr)+NaCl \quad (1)$$

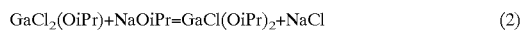

$$GaCl_2(OiPr)+NaOiPr=GaCl(OiPr)_2+NaCl \quad (2)$$

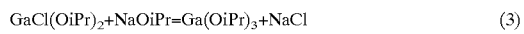

$$GaCl(OiPr)_2+NaOiPr=Ga(OiPr)_3+NaCl \quad (3)$$

In case where the reaction completely proceeds according to the formulas, the reaction of $GaCl_3$ with NaOiPr equivalent thereto is to produce $Ga(OiPr)_3$ without leaving $GaCl(OiPr)_2$. However, in spite of the presence of excessive NaOiPr, the reaction of formula (3) practically seems difficult to finish, and it is presumed that a small amount of $GaCl(OiPr)_2$ remains and contaminates $Ga(OiPr)_3$ of the desired product. The removal of $GaCl(OiPr)_2$ by distillation is difficult. It is known that $Ga(OiPr)_3$ exists as a dimer $[Ga(OiPr)_3]_2$. On the other hand, it is presumed that $GaCl(OiPr)_2$ exists as a complex $Ga(OiPr)_3$—$GaCl(OiPr)_2$, and close boiling points of the dimer and the complex make it difficult to separate $GaCl(OiPr)_2$ by distillation.

The inventors have found that potassium isopropoxide (hereinafter represented by KOiPr) is added to $Ga(OiPr)_3$ containing a small amount of $GaCl(OiPr)_2$ to allow the reaction between both isopropoxides, subsequently $Ga(OiPr)_3$ is recovered by distillation, and thereby the chlorine amount in the $Ga(OiPr)_3$ can be decreased to approximately 0.02 percent with ease. Use of NaOiPr completely fails to exert this effect of KOiPr. Use of LiOiPr causes the gelation of the greater part of the reaction product to make difficult the recovery of the product by distillation. Of the alkali metal alkoxides, this major effect of KOiPr has not been forecasted at all.

The gallium alkoxides in the invention are compounds recovered by sublimation or distillation. Examples of such compounds include gallium isopropoxide, gallium methoxide, gallium ethoxide, gallium n-propoxide, gallium n-butoxide, gallium s-butoxide, and gallium t-butoxide. Of these, gallium isopropoxide has a high vapor pressure, can be distilled with ease, and used as a raw material for other gallium alkoxides. The gallium isopropoxide is, therefore, the most important as a target of the invention.

A potassium alkoxide used in the invention preferably is the same alkoxide as a gallium alkoxide to be purified. For example, for the purification of gallium isopropoxide, potassium isopropoxide is used. This can protect the gallium isopropoxide from contamination with another gallium alkoxide.

The amount of a potassium alkoxide used in the invention preferably ranges from 1 to 3 equivalents to the amount of the impurity chlorine. Although the amount of the potassium alkoxide is theoretically 1 equivalent thereto, the amount most preferably ranges from 1.1 to 1.5 equivalents in view of the reaction rate or the analytical error of chlorine. The addition of 3 equivalents or more of the potassium alkoxide fails to further reduce the amount of the impurity chlorine in a gallium alkoxide recovered by sublimation or distillation, and unpreferably leads to a serious decrease in the yield of the gallium alkoxide. The cause of the decrease in the yield may be attributed to the formation of a complex from the gallium alkoxide and the excess potassium alkoxide to cause great decrease in vapor pressure. Since the potassium alkoxide forms such complex, the gallium alkoxide recovered is not contaminated by impurity potassium.

The organic solvents used in the invention need to be those inactive to the gallium alkoxides, and preferred solvents are selected from toluene, xylene, alkanes having 6 to 10 carbon atoms, and cycloalkanes having 6 to 10 carbon atoms. The alkanes having 6 to 10 carbon atoms include hexane, heptane, octane, and decane. The cycloalkanes having 6 to 10 carbon atoms include cyclohexane.

The gallium alkoxides dissolve in these hydrocarbons such as toluene and octane more than in alcohols themselves forming the gallium alkoxides. Although the potassium alkoxides only slightly dissolve in the hydrocarbons such as toluene and octane, the alkoxides seem to dissolve well therein in the co-presence of the gallium alkoxides so that the reaction with the chlorine compounds proceeds with ease. Use of the hydrocarbon solvents makes it easiest to distill away the solvents from reaction solutions and preferably promises high yields of the gallium alkoxides by simple distillation.

On the other hand, use of the alcohols themselves forming the gallium alkoxides as the solvents for the reaction seems to cause slight gelation of the reaction solution, and slightly decreases the yields of the gallium alkoxides by simple distillation, although the effect of decreasing the chlorine content is maintained.

The reaction of the invention is carried out in an organic solvent with stirring at a reflux temperature of 70 to 140° C. for 1 to 8 hours. After the reaction is complete, the solvent was distilled away at atmospheric pressure and then under reduced pressure, and subsequently a gallium alkoxide is recovered under reduced pressure by distillation or sublimation. The gallium alkoxides have relatively high heat stability to facilitate the recovery thereof.

The gallium alkoxides useful as the raw materials of the formation of dielectrics containing gallium oxide and as the raw materials of the syntheses of compounds for photoelectronics can be decreased in the amount of the impurity chlorine contained therein from approximately 1% to approximately 0.02% by the process of the invention.

EXAMPLE 1

$Ga(OiPr)_3$ synthesized by the reaction of NaOiPr with $GaCl_3$ and recovered by distillation was used as a raw material, and an experiment to decrease the chlorine content was carried out. Analysis of the $Ga(OiPr)_3$ revealed that the chlorine content was 0.98 weight percent.

In a 500-ml four-necked flask equipped with a reflux condenser, a thermometer, and a stirrer, 50.0 grams of $Ga(OiPr)_3$ containing 0.98 weight percent of chlorine [0.20 mole as $Ga(OiPr)_3$ and 0.014 mole as chlorine], 2.0 grams of KOiPr (0.020 mole; 1.4 equivalent to chlorine), and 400 ml of toluene were placed in an atmosphere of argon replaced under vacuum. Subsequently, the temperature was raised with stirring, and the reaction was continued at reflux conditions for 5 hours. Thereafter, the solvent was thoroughly distilled away under vacuum. The residue was simply distilled at 0.3 Torr and, 44.0 grams (0.178 mole) of $Ga(OiPr)_3$ was obtained as a colorless, transparent distillate at approximately 110° C. The yield was 89%. This liquid became a white solid after two days. Found values in elementary analyses: gallium: 28.3% (Calculated value: 28.3%), chlorine: 0.022%, and potassium: 6 ppm. The result shows that the treatment with KOiPr decreases the chlorine content from 0.98% to 0.022%.

EXAMPLE 2

Operations similar to those in Example 1 were carried out except that the amount of KOiPr used in Example 1 was increased to 4.0 grams (0.041 mole; 2.9 equivalent to chlorine). The amount of $Ga(OiPr)_3$ recovered by simple distillation was 40.5 grams (0.164 mole). The yield was 81%. Found values in elementary analyses: gallium content: 28.4%, chlorine: 0.021%, and potassium: 6 ppm. This result reveals that the effect of KOiPr is observed, but increase in the amount of the KOiPr only causes the chlorine content to decrease to 0.021% and rather invites decrease in the yield.

Comparative Example 1

Operations similar to those in Example 1 were carried out except that KOiPr added in Example 1 was replaced by 3.3 grams (0.040 mole; 2.9 equivalent to chlorine) of NaOiPr. $Ga(OiPr)_3$ recovered by simple distillation was 36.6 grams (0.148 mole), and the yield was 74%. Found values in elementary analyses: gallium content: 28.3%, chlorine: 0.96%, and sodium: 1 ppm. This result reveals that the effect of NaOiPr added was not seen at all.

Comparative Example 2

Operations similar to those in Example 1 were carried out except that KOiPr used in Example 1 was replaced by 2.7 grams (0.041 mole; 2.9 equivalent to chlorine) of LiOiPr. The mixture was a solution at 20 to 50° C., but when kept in a reflux temperature, the whole of the mixture formed a colorless, transparent gel, which made it difficult to stir the whole. After the reflux was continued for 5 hours, the removal of the solvent and the distillation of $Ga(OiPr)_3$ were attempted, but violent bumping made impossible the normal recovery of the product. It has been found that a series of operations cannot be normally carried out by use of LiOiPr.

What is claimed is:

1. A process for purifying a gallium alkoxide by adding a potassium alkoxide to the gallium alkoxide containing a chlorine compound as an impurity to allow reaction in an organic solvent and subsequently recovering the gallium alkoxide by distillation or sublimation.

2. The process according to claim 1 wherein the gallium alkoxide is gallium isopropoxide and the potassium alkoxide is potassium isopropoxide.

3. The process according to claim 1 or 2 wherein an amount of the potassium alkoxide is 1 to 3 equivalent to an amount of the impurity chlorine.

4. The process according to claim 1 or 2 wherein the organic solvent is a compound selected from toluene, xylene, alkanes having 6 to 10 carbon atoms, and cycloalkanes having 6 to 10 carbon atoms.

5. The process according to claim 3 wherein the organic solvent is a compound selected from toluene, xylene, alkanes having 6 to 10 carbon atoms, and cyclohexanes having 6 to 10 carbon atoms.

* * * * *